United States Patent [19]

Wrede et al.

[11] Patent Number: 4,971,669

[45] Date of Patent: Nov. 20, 1990

[54] PROCESS AND DEVICE FOR THE CONTINUOUS VAPORIATION OF VOLATILE ACTIVE COMPOUNDS

[75] Inventors: Wolfgang Wrede, Holzminden; Norbert Rohde, Deensen, both of Fed. Rep. of Germany

[73] Assignee: Haarmann & Reimer GmbH, Holzminden, Fed. Rep. of Germany

[21] Appl. No.: 300,672

[22] Filed: Jan. 23, 1989

[30] Foreign Application Priority Data

Feb. 6, 1988 [DE] Fed. Rep. of Germany ....... 3803665

[51] Int. Cl.⁵ .............................................. C25B 1/00
[52] U.S. Cl. .................................. 204/129; 204/59 R; 204/101; 204/263; 204/265; 204/266; 55/83; 55/84; 55/244; 239/337; 239/339; 239/373; 239/6
[58] Field of Search ..................... 204/59 R, 128, 129, 204/263, 265–266, 291, 101; 239/6, 337, 339, 373; 55/84, 83, 244; 102/367

[56] References Cited

U.S. PATENT DOCUMENTS 4,418,623 12/1983 Gauchard ........................... 102/369
4,726,888 2/1988 McCambridge .................... 204/129

FOREIGN PATENT DOCUMENTS 2486421 1/1982 France ................................ 239/339

Primary Examiner—John F. Niebling
Assistant Examiner—Kathryn Gorgos
Attorney, Agent, or Firm—Sprung Horn Kramer & Woods

[57] ABSTRACT

The invention relates to a process for the vaporization of volatile active compounds and mixtures of active compounds according to which the active compound or the mixture of active compounds is conveyed from its storage vessel by the use of an electrolytically produced gas stream into the room which is to be supplied with a vaporizing mixture of active compounds, and is there caused to vaporize directly or by the use of inert vaporizers.

6 Claims, 1 Drawing Sheet

PROCESS AND DEVICE FOR THE CONTINUOUS VAPORIATION OF VOLATILE ACTIVE COMPOUNDS

BACKGROUND OF THE INVENTION

1. Field of The Invention

The invention relates to a new process for the continuous vaporization of volatile active compounds, in particular perfume oils, and to a device for carrying out the process.

1. Description of Related Art

Various processes for the continuous vaporization of volatile active compounds, for example perfume oils, are already known. These processes known at the present time are based on attempting to achieve the most uniform release possible of the active compounds to the ambient air either by increasing the surface or by raising the temperature of the substances to be vaporized. In order to increase their surface, the active compounds have been applied, for example, to carriers, such as filter paper, nonwovens, foamed sheets of plastic or powders composed of inorganic materials, for example gypsum powder, or have been incorporated into carriers such as gelatine, crosslinked celluloses, waxes, polyvinyl chloride or ethylene/vinyl acetate copolymers (see, for example, U.S. Patent Specification Nos. 2,927,055 and 3,945,950; and German Offenlegungsschriften Nos. (German Published Specifications) 2,454,969, 2,521,265 and 2,606,544). Increasing the temperature has been effected by supplying heat to the storage vessels containing the active compounds to be vaporized.

These known processes have, however, the serious disadvantage that, even if the individual components of the process are carefully matched, for example the carrier to the active compounds to be vaporized, vaporization does not proceed at a linear rate, at least over prolonged periods of time, but the amount of active compound released to the surroundings per time unit during the varporization operation varies and—in the case of mixtures of substances to be vaporized—the composition of the gaseous mixture of substances also varies. In addition, quantitative vaporization of the active compounds to be vaporized is not achieved in practice, but vaporization residues are formed, and these can amount to up to 15% by weight of the amount of active compound to be vaporized.

Since, in practice, both a constant release of substance and a constant composition of the mixtures of substances to be vaporized are required for deodorizing the air in a room and for disinfecting the room and the like, the object was, therefore, to find a process by means of which linear vaporization of the active compound$ and mixtures of active compounds to be vaporized is obtained.

SUMMARY OF THE INVENTION

It has been found, surprisingly, that such a linear vaporization of volatile active compounds and mixtures of active compounds is obtained in a simple manner by conveying the active compounds or mixtures of active compounds to be vaporized from their stock vessels by means of a gas produced electrolytically.

It has been found that both very small and very large, constant and exactly reproducible amounts of gas can be produced electrolytically, and that exactly reproducible amounts of active compounds can also be conveyed from the stock vessels and vaporized by means of these exactly reproducible amounts of gas. A stream of gaseous active compounds which is constant both in respect of time and in its composition, and hence, the desired linear vaporization of the volatile active compounds and mixtures of active compounds is achieved, in accordance with the invention, by means of the electrolytically produced stream of gas.

The invention, therefore, relates to a process for the vaporization of volatile active compounds and mixtures of active compounds, which is characterized in that the active compound or the mixture of active compounds is conveyed from its storage vessel by means of an electrolytically produced gas stream into the room which is to be supplied with a vaporizing mixture of active compounds, and is there caused to vaporize directly or by means of inert vaporizers, that is to say; vaporizers which do not undergo any interaction with the active compounds.

BRIEF DESCRIPTIONS OF THE DRAWINGS

FIG. 1 schematically depicts the process according to the invention.

FIG. 2 schematically shows in detail a storage vessel as depicted in FIG. 1.

DESCRIPTION OF PREFERRED EMBODIMENTS

The electrolytic production of gases, for example hydrogen, oxygen and oxyhydrogen gas (a 2:1 mixture of $H_2/O_2$) is known (see Hoffmann's apparatus for the decomposition of water). In the electrolysis of water, hydrogen is evolved at the cathode and oxygen is evolved (as a secondary product) at the anode. Either the hydrogen or the oxygen can be used in accordance with the invention as the conveying gas; for reasons of simplicity, however, it is preferable to use directly the oxyhydrogen gas which is formed in the course of the electrolysis.

The amounts of gas (m) evolved can be calculated directly by means of Faraday's law:

$$m = I \times A \times t.$$

(A = electrochemical equivalent; I = strength of current; t = time).

The electrochemical equivalents A for hydrogen, oxygen and oxyhydrogen gas are as follows:

$O_2$: 0.0829 [mg] = 0.058 [N cm$^3$/ampere-second]
$H_2$: 0.01044 [mg] = 0.117 [N cm$^3$/ampere-second]
oxyhydrogen gas 0.09334 [mg] = 0.174 [N cm$^3$/ampere-second].

The amount of active compound [ml] conveyed from the storage vessel by this amount of gas follows immediately from the amounts of electrolytically produced gas which can be calculated by Faraday's law. In this manner, it is possible to calculate immediately, from the electrical energy (strength of current × time) supplied via the electrolysis, the amount of active compound [ml] which vaporizes or to calculate, from the amount of active compound which it is desired to vaporize, the amount of gas [ml] required and from the latter the electrical energy required.

Figure 1:
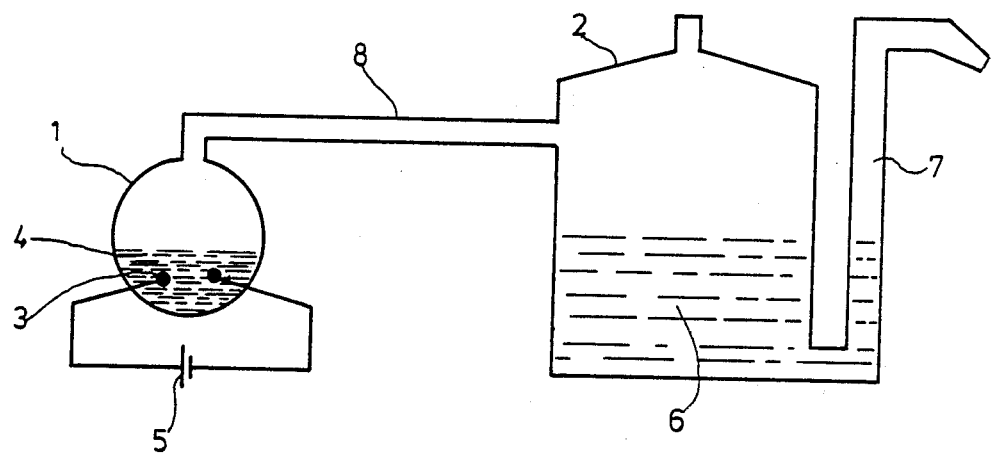

A device which, in principle, consists only of an electrolytic cell for the production of the conveying gas (oxyhydrogen gas) and of a storage vessel wherein the active compound or the mixture of active compounds to be vaporized is located is required for carrying out the process according to the invention. The principle of such a device for carrying out the process according to the invention is shown in FIG. 1. In this FIG. 1, (1) denotes the electrolytic cell and (2) denotes the storage vessel for the active compound to be vaporized. The electrolytic cell contains 2 electrodes (3) and water acidified with, for example, $H_2SO_4$, (4). Element (5) is the source of current with which the cell is operated. The oxyhydrogen gas evolved in the course of the electrolysis is introduced into the storage vessel (2) via the line (8). In this storage vessel, the gas exerts a pressure on the surface of the volatile active compound (6) or solution of the active compound to be vaporized and conveys it in this manner through the exit line (7) into the room to be supplied with the vaporizing mixture of active compounds.

The dimensions of the electrolytic cell and the storage vessel are given by the amount of the (mixture of) active compound(s) which is to be released to the surroundings within the time unit and by the intervals at which this device is to be serviced (refilling the active compound to be vaporized and refilling the water to be electrolyzed). The calculation of the dimensions of the electrolytic cell and the storage vessel may be illustrated by means of the following example:

For example, the air in a room (for example a waiting room in a medical practice (dimensions of room: $7 \times 4 \times 2.30 \ m^3 = 64.5 \ m^3$) is to be deodorized. For this purpose, it is intended to vaporize 0.06 ml of perfume oil within the room per time unit (for example per hour). An amount of 0.06 ml of oxyhydrogen gas is required for the vaporization of this amount, and accordingly, an electrical energy of (strength of current × time) 0.34 As is required (at a voltage required for the electrolysis of the water of ~ 1.8 to 3.0 volts).

Figure 2:
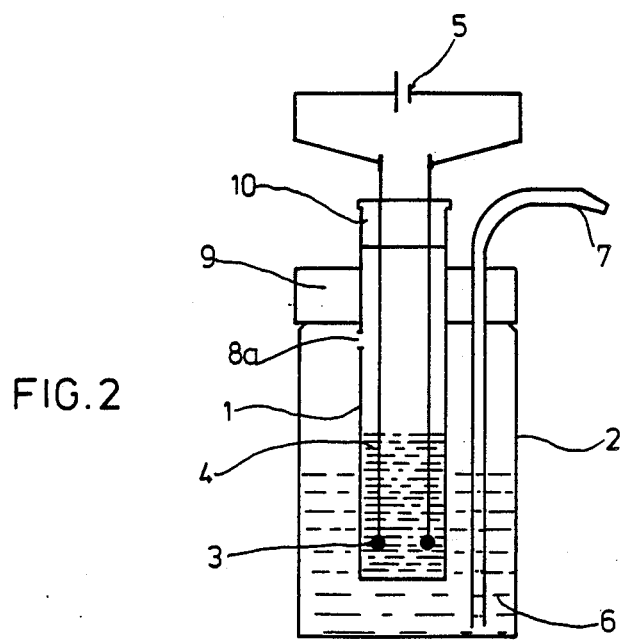

In this case, the particularly handy and practical device described in FIG. 2 could be used as a deodorizer for the air in the room. It consists of a storage vessel (2) (volume: 30 ml) into which a small electrolytic cell (1) has been inserted concentrically (volume of the electrolytic cell: 3 ml; size of the individual electrodes (3): ~ 5 $mm^2$; electrode material: Pt; and amount of electrolyte (water acidified with $H_2SO_4$): 2 ml). The gas formed in the electrolytic cell passes through the gas outlet orifice (8a) into the storage vessel (2) and forces the perfume oil (6) out of the latter into the room through the outlet capillary (7) for the active compound.

Gastight closure of the electrolytic cell (1) is achieved by means of the seal (10), and of the storage vessel (2) by means of the seal (9). The seal (10) serves at the same time as a mounting for the electrodes (3) and for the supply of current.

The amounts of active compound to be vaporized depend on its effectiveness (in the case of perfume oils on the intensity of odor). In the case of perfume oils, the amounts to be used for deodorizing the air in the room are, according to the invention, about 50 to 100 ml of perfume oil per room for a period of 4 to 8 weeks, that is to say ~ 0.06 ml per room and per hour.

The energy required for the electrolytic production of the conveying gas can be supplied to the electrolytic cell from customary sources of current, for example from batteries or from sources of direct current fed from the mains. The voltage required for the electrolysis of the water is, in theory, 1.23 volts, but in practice, voltages of 1.8 to 2.6 volts are required. Two batteries each of 1.5 volts and having a capacity of 1 ampere-hour make it possible to produce 627 ml of oxyhydrogen gas and hence, to vaporize 627 ml of active compound.

Owing to the low consumption of energy, it is also possible to use solar batteries as sources of current. These batteries are particularly advantageous if it is desired to vaporize the active compounds only in the presence of light; that is to say when the rooms are occupied.

The active compound conveyed from the storage vessel can either be allowed to vaporize directly or can be distributed within the room by means of customary inert vaporizers, that is to say, vaporizers which do not undergo any interaction with the active compounds to be vaporized, for example plates gently fluttered by fans. Vaporization of the active compounds at a linear rate is achieved both in the case of indirect and in the case of direct vaporization.

Volatile active compounds or mixtures of active compounds are to be understood, within the scope of the process according to the invention, as active compounds and mixtures of active compounds which, at room temperature, have a certain vapor pressure required for vaporization or in which the required vapor pressure can be produced by heating. Examples of volatile active compounds (compound mixtures) are insecticides, such as (DDVP), lindane and dieldrin; disinfectants, such as diethylene glycol and triethylene glycol; and, in particular, perfume oils. Perfume oils are mixtures of compounds in which the components differ in most cases in their vapor pressures. The process according to the invention makes it possible for the first time to vaporize perfume oils over a prolonged period of time without the occurrence of a change in the odor note of the oils. The odor note of a perfume oil vaporized by means of the process according to the invention is constant from the vaporization of the first drop to the vaporization of the last drop. In the vaporization processes used hitherto, the more readily volatile components have determined the odor note of the perfume oil vaporized at the start of the vaporization, whereas towards the end of the vaporization the more sparingly volatile constituents have determined the odor note.

EXAMPLE

The device described below is used for spraying 6.2 ml per hour of a perfume oil, that is an amount of perfume oil which is sufficient for deodorizing the air of large rooms (rooms having a volume of 5,000–10,000 $m^3$) e.g. rooms for events, such as theaters or concert halls and open-plan offices; it is constructed in principle like the device described in FIG. 2.

Description of the electrolytic cell (1) which is concentrically inserted into the storage vessel (2): (Glass bottle, diameter: 15 mm; height: 60 mm; electrolyte: 3 ml of water acidified with a few drops of sulfuric acid; size of the individual platinum electrodes (3): ~ 5 $mm^2$). The electrode connections pass through the plug lid (10) which closes the glass bottle in a gastight manner and are connected to a solar cell (dimensions: $90 \times 90$ mm; maximum voltage: 3 volts; maximum current strength: 0.01 amperes).

During electrolysis, 6.2 ml per hour of oxyhydrogen gas are formed in this cell. The gas enters the gas space of the storage vessel (2) through the outlet orifice (8a).

Description of the storage vessel (2):

A wide-neck 100 ml glass bottle equipped with a screwed lid (9) and filled with 75 mol of perfume oil (6). This glass bottle is furthermore equipped with a steel capillary (7) (diameter: 0.25 mm) which acts as an exit line. This capillary extends to just above the base of the wide-neck glass bottle and passes out through the screwed lid.

By means of the 6.2 mol of oxyhydrogen gas produced per hour, 6.2 ml of perfume oil per hour are conveyed out of the storage vessel through the capillary to the inert surface of a vaporizer and are allowed to vaporize thereon.

What is claimed is:

1. A process for the linear continuous vaporization of volatile active compounds and mixtures of active compounds, which process comprises continuously conveying the active compound of the mixture of active compounds from a storage vessel containing the active compound or mixture of active compound by means of an electrolytically produced gas into a room which is to be supplied with a vaporizing active compound, and allowing the active compound or mixture of active compounds to vaporize in said room directly or by means of an inert vaporizer.

2. The process of claim 1, wherein the gas produced electrolytically is oxyhydrogen gas.

3. The process of claim 1, wherein the active compound or the mixture of active compounds is a perfume oil.

4. The process of claim 1, wherein the active compound or mixture of active compounds conveyed from the storage vessel into the room to be applied with a vaporizing active compound is distributed within the room by means of an inert vaporizer.

5. A device for carrying out the process according to claim 1, comprising an electrolytic cell and a storage vessel for the active compound or mixture of active compounds to be vaporized.

6. The device of claim 5, wherein the electrolytic cell contains two electrodes and water which has been acidified with sulfuric acid, and the oxyhydrogen gas evolved in the electrolysis is introduced via a line into the storage vessel and there exerts pressure on the surface of the active compound or mixture of active compounds of the solution of active compound to be vaporized and conveys the active compound through an exit line into the room to be supplied with the vaporizing active compound or mixture of active compounds.

* * * * *

UNITED STATES PATENT AND TRADEMARK OFFICE
CERTIFICATE OF CORRECTION

PATENT NO. : 4,971,669

DATED : November 20, 1990

INVENTOR(S) : Wrede et al.

It is certified that error appears in the above-identified patent and that said Letters Patent is hereby corrected as shown below:

Title Page      [54] Title 2nd line delete " VAPORIATION " and substitute -- VAPORIZATION --

Col. 1, line 2 of Title      Delete " VAPORIATION" and substitute -- VAPORIZATION --

Signed and Sealed this

Twenty-fifth Day of August, 1992

*Attest:*

DOUGLAS B. COMER

*Attesting Officer*      *Acting Commissioner of Patents and Trademarks*